US00PP14337P39

(12) United States Plant Patent
Jarmin

(10) Patent No.: US PP14,337 P3
(45) Date of Patent: Dec. 2, 2003

(54) CRABAPPLE TREE NAMED 'JARMIN'

(50) Latin Name: *Malus sylvestris*
Varietal Denomination: Jarmin

(76) Inventor: Marvin Jarmin, 16866 Donnelly Rd., Mount Vernon, WA (US) 98273

( * ) Notice: Subject to any disclaimer, the term of this patent is extended or adjusted under 35 U.S.C. 154(b) by 125 days.

(21) Appl. No.: 09/997,044

(22) Filed: Nov. 28, 2001

(65) Prior Publication Data

US 2003/0101491 P1 May 29, 2003

(51) Int. Cl.[7] ..... A01H 5/00

(52) U.S. Cl. ..... Plt./173
(58) Field of Search ..... Plt./173

(56) References Cited

PUBLICATIONS

Disclosure Letter by Marvin Jarmin.

*Primary Examiner*—Bruce Campell
(74) *Attorney, Agent, or Firm*—Klarquist Sparkman LLP.

(57) ABSTRACT

The 'Jarmin' crabapple is a non-fruiting crabapple tree, with an upright growth habit, attractive pink bloom with semi-double and double flowers being typical, and foliage resistant to both apple scab (*Venturia inaequalis*) and powdery mildew (*Podosphaera leucotricha*).

4 Drawing Sheets

Botanical designation: *Malus sylvestris* Mill.

BACKGROUND

The present invention relates to a new and distinct variety of crabapple (*Malus sylvestris*, Mill.) which I have named 'Jarmin', which grew from a seedling of unknown parentage and was found in cultivated area in Puyallup, Wash. The seed which resulted in this seedling was planted in approximately 1978. The original tree was transplanted to my residence in Mount Vernon, Wash. in 1982 and has remained in the same location since that time (approximately 19 years).

The first asexual propagation of this new variety occurred in 1995, when two experimental trees were propagated by grafting buds on M26 rootstock in Mount Vernon, Wash. and subsequently were planted in a block of 45 crabapple varieties at the Washington State University Research Unit, Mount Vernon, Wash. These trees have flowered four times since planting, which confirmed that their growth habits and flowering characteristics were identical to those of the original tree. Subsequently, in 1998, approximately an additional 100 buds were grafted on seedling rootstock in Mount Vernon, Wash. These trees flowered in the nursery row in the second season (FIG. 4) and were identical to the original tree.

DETAILED DESCRIPTION

The detailed description that follows is based on observations of the original trees and progeny thereof located at several locations in Mount Vernon, Wash. All of these sites are within five miles of each other in the alluvial plain of Skagit Valley, in western Washington state. This area has a coastal climate characterized by cool, dry summers and mild, rainy winters, and an annual rainfall of 32 inches. The performance of this new variety in other areas with a more severe climate or lacking in winter chilling is not known.

Color descriptions (hue/value/chroma) are from the Munsell Book of Color, Kollmorgen Instruments Corp., 405 Little Britain Road, New Winsor, N.Y. 12553. Color would vary with lighting conditions under which photographs are taken and is also expected to vary somewhat under different growing conditions.

THE PLANT

Tree

Parentage: Original tree is a seedling of unknown parentage which grew from seed planted in a cultivated area in Puyallup, Wash.

Tree size: Medium, height of original seedling tree at 19 years 7 to 8 m, width 2 to 3 m.

Vigor: Low, average seasonal growth over 19 years approximately 20 cm.

Chilling requirements: Unknown.

Productivity: Prolific, precocious flowering; total absence of fruit, although flowers have both stamen and pistil.

Trunk

Figure 2:
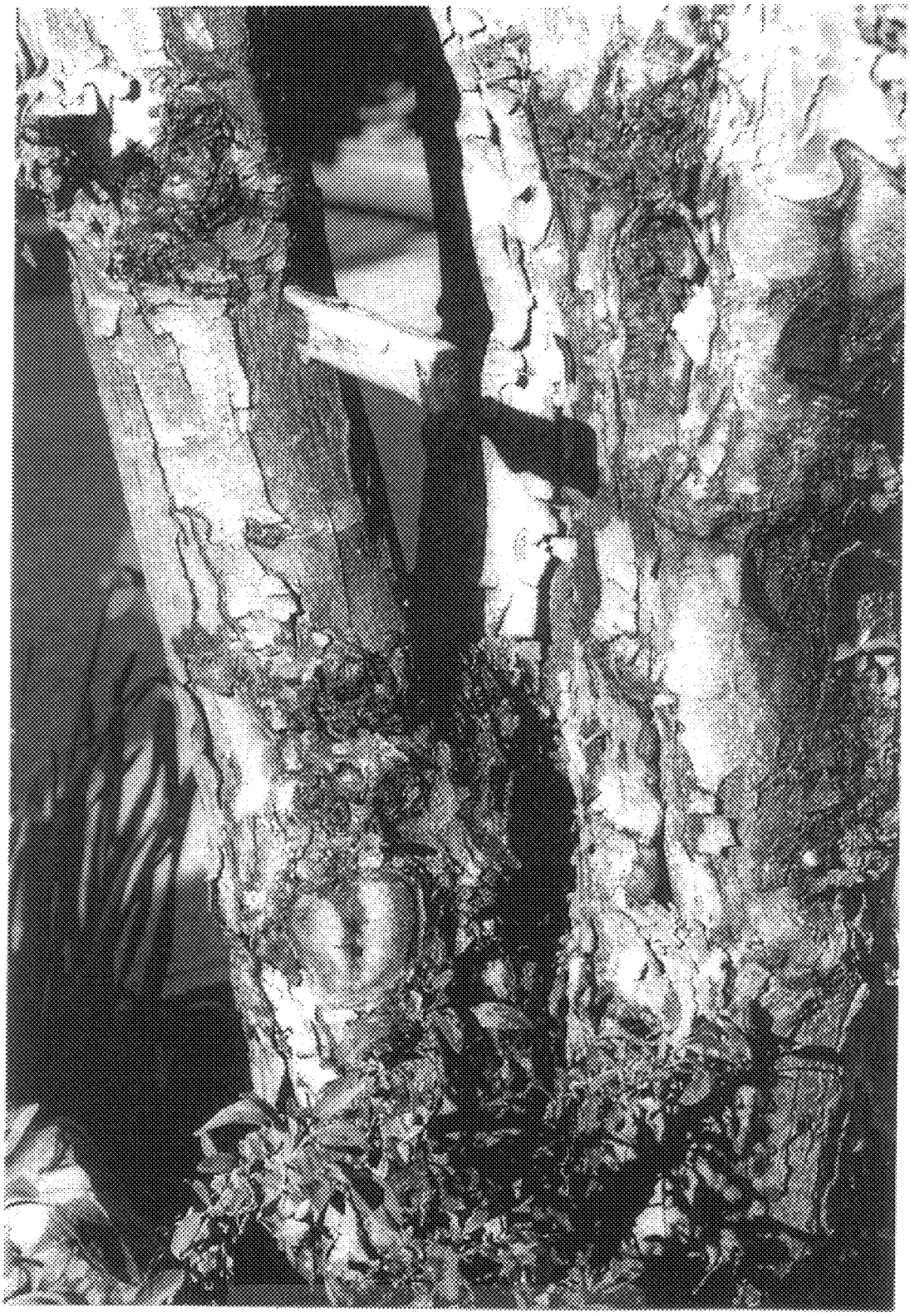
FIG. 2 is a photograph of the trunk and bark of original tree and was taken about Apr. 20, 2001. This photograph shows vertical cracking of the mature bark.
Figure 3:
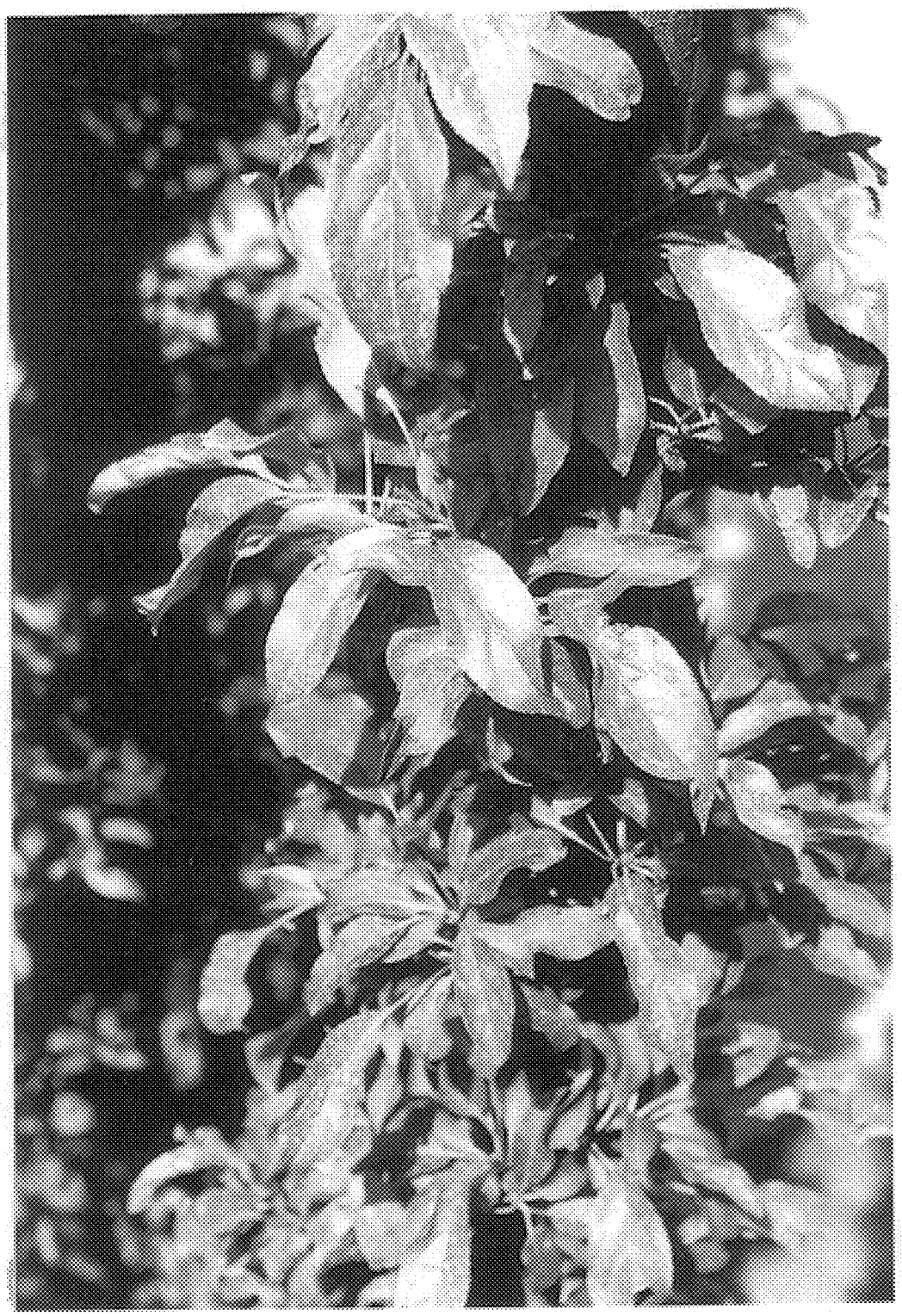
FIG. 3 is a photograph of foliage of the 'Jarmin' crabapple in midseason (June 2001). No evidence of disease infestation has been observed though no fungicides have ever been applied to this photographed tree.

Size and texture: Original tree stocky, approximately 52 cm in diameter at 0.5 m from ground line at 19 years. Texture smooth, with deep vertical furrows at approximately 4 cm intervals (FIG. 2).

Color: Mature bark color 7.5 YR 3/4 (reddish-brown) to grey-brown 2.5Y 5/4.

Branches

Figure 1:
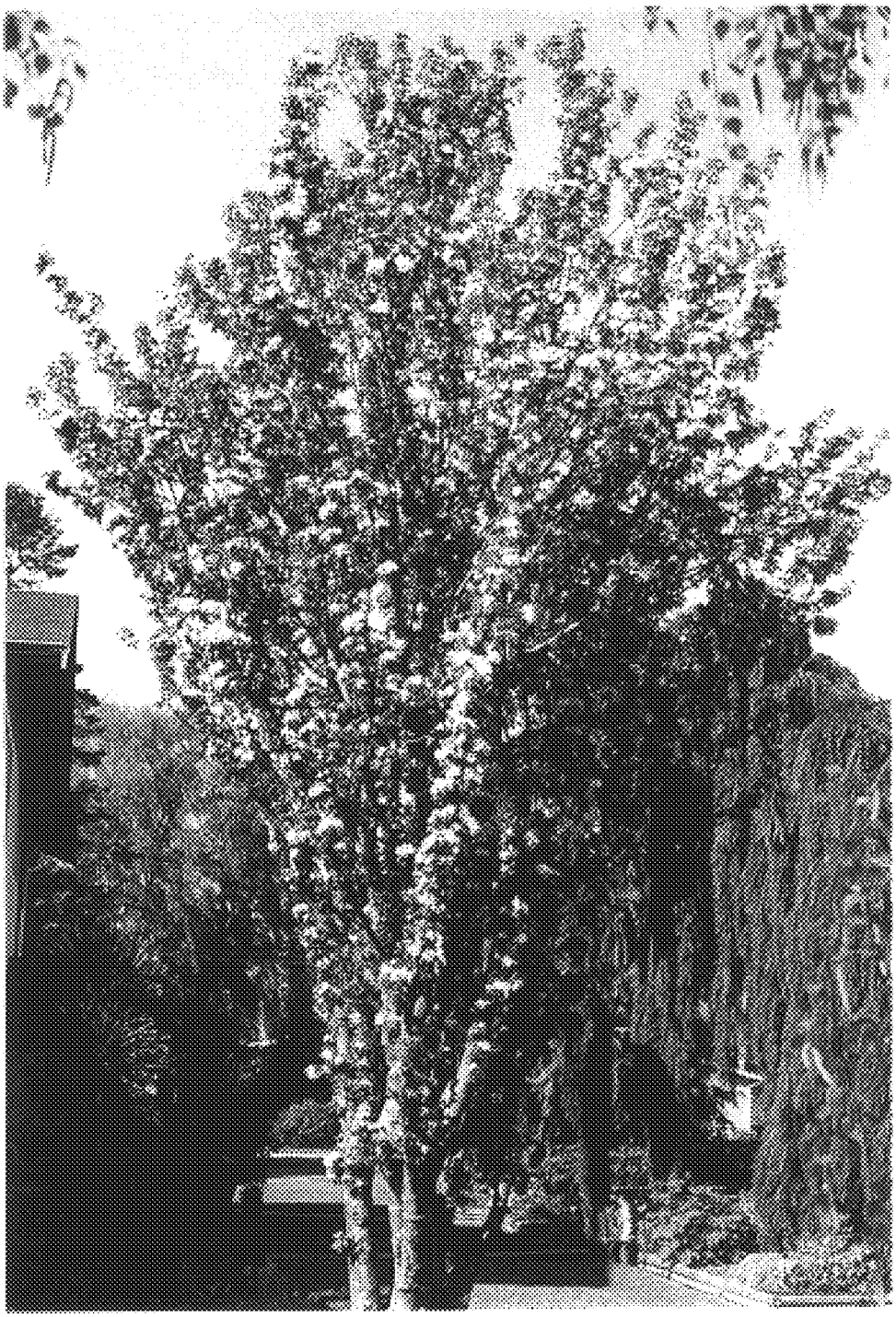
FIG. 1 is a photograph of the original tree in full bloom on about Apr. 26, 2001 in Mt. Vernon, Wash.

Habit: Distinctly upright, heavily spurred, stout. Two year old branches growing in Mount Vernon, Wash. were about 20 mm in diameter. Branches angle at emergence from main trunk typically 30 degrees or less from the vertical. The overall habit of the tree is columnar to inverted pyramidal (FIG. 1), unlike typical crabapple trees, which are usually round-headed or spreading.

Size and texture: Branches typically heavy caliper in relation to length; smooth texture. For example, 2 year old branches in some samples were 52 cm in length and 20 mm in diameter.

Color: Bark color of one-year dominant shoot—7.5 R 3/4 (reddish-brown); two-year old branch—7.5 R 4/2 (grey-brown).

Pubescence: Glabrous, except at branch tips. Branch tips have fine hair which is colorless.

Lenticels: One-year wood—almost lacking lenticels, extremely small (<0.2 mm); more numerous on two-year wood; still inconspicuous, with a density of less than 4 per sq. cm., almost colorless.

Leaves

Size: Medium, leaf blade length 6.1 cm, width 3.2 cm, petiole 2.8 cm (average of 10 leaves); measured at Mount Vernon, Wash., May 2001.

Form: Long, oblong.

Color:

*Upwardly disposed surface.*—5 GY 4/6.

*Downwardly disposed surface.*—5 GY 5/6.

*Vein.*—2.5 GY 7/6.

Marginal:

Form: Finely crenate.

Tip: Obtuse (100 degrees) to acute (60 degrees).

Stipules: Mostly lacking; where found (less than 10% of leaves), they are small, approximately 6 mm in length, 0.5 mm in width.

Pubescence: Upper surface—very sparse pubescence along primary veins; color 2.5 GY 9/4. Lower surface—almost glabrous except along midrib and primary veins; Lower surface pubescence appears colorless. Petiole has very fine, colorless pubescence along its entire length.

Petiole: Medium to stout, 30.5 mm long and 2 mm in diameter (average of 10 leaves), measured at Mount Vernon, Wash., October 2001. Color of petiole 2.5 GY 7/6.

Flowers

Time of bloom:

2001, at Mount Vernon, Wash.—First Bloom April 18. Second Bloom April 28. Petal Fall May 28.

This is considered mid-season blooming, and corresponded with bloom period of 'Jonagold' (not patented), 'Gala' (U.S. Plant Pat. No. 3,637 (Expired)), 'Braeburn' (not patented) apples and 'Snowdrift' (not patented) crabapple.

Bloom:

Description: Flowers generally in clusters of 5 to 8 flowers per spur or peduncle. Individual flowers are up to 45 mm in diameter when fully open. Flower have from 5–10 petals, average of 8 petals.

Buds

Figure 4:
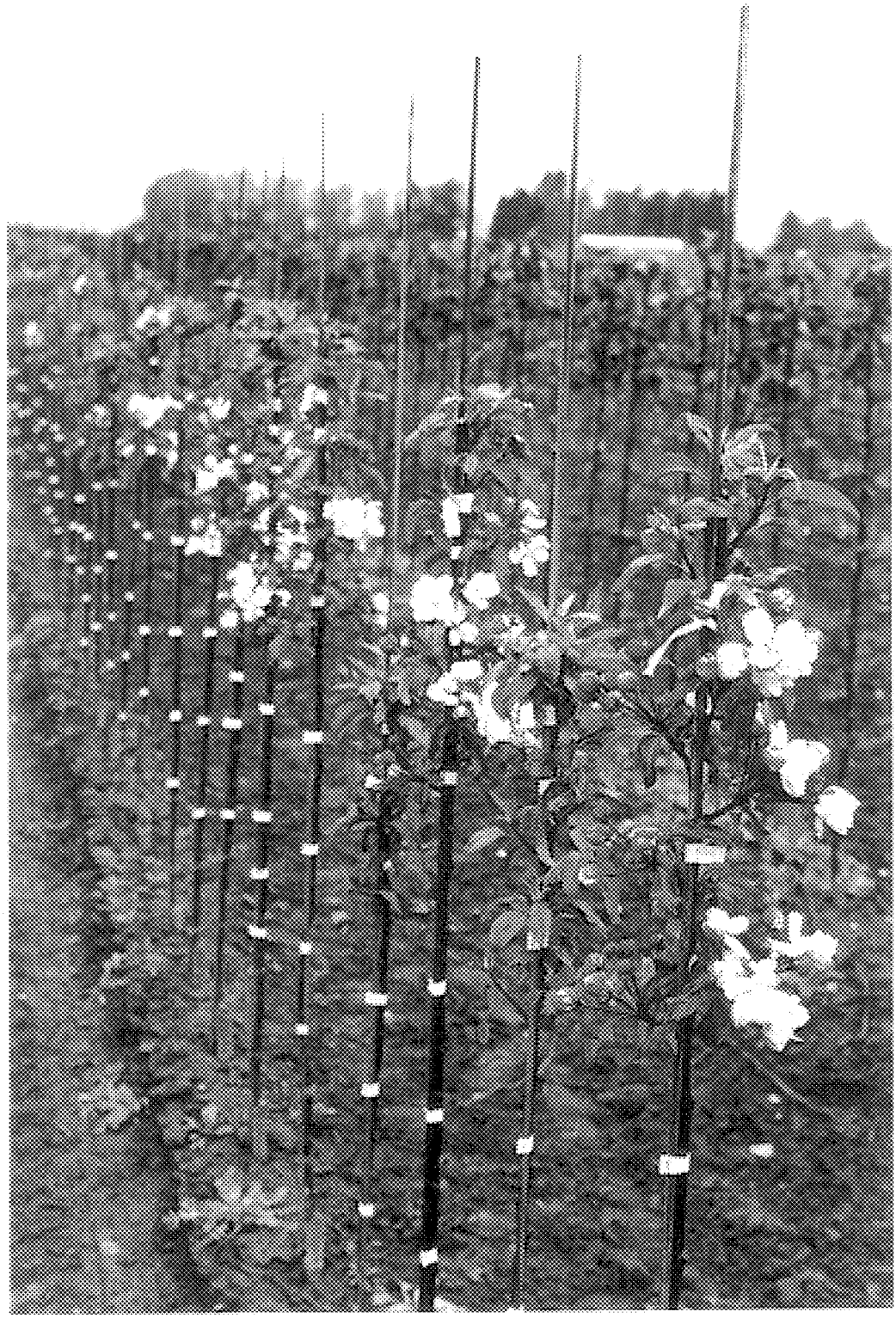
FIG. 4 is a photograph of 'Jarmin' crabapple trees which were grafted in 1998 and was taken in the spring of 2001. This photograph shows the precocious flowering habit and uniformity in growth habit of the new tree.

Size: In popcorn stage, buds vary in size with their development (FIG. 4); When mature in Mount Vernon, Wash., a typical bud has been observed in 2001 to be about 25 mm long by 20 mm in diameter at widest part immediately prior to opening; color 2.5 R 5/6 (pinkish-red).

Open Flowers

Size: Individual petals widely variable in size and shape, a sampling of petals observed in Mount Vernon, Wash., in April of 2001, averaged 25 mm in length, 15 mm in width and were generally oval in shape; sometimes attached on a long stalk or claw up to 10 mm in length. Individual flowers in a sampling at the same location were observed to be up to 45 mm in diameter when fully open. The flowers of this variety are distinct from almost all fruiting apple varieties and from most crabapple varieties in that they typically have semi-double flowers with 5 primary petals and 5 somewhat smaller inside petals. In a Washington State University trial of 45 crabapple varieties, only one, 'Pink Cloud' (not patented) had double flowers. Other characteristics, however, e.g., round tree shape and flower of color 'Pink Cloud', clearly distinguished the new variety from 'Pink Cloud' any other that was in the trial.

Surface texture: Smooth.

Color: Upper surface pure white when fully open, with occasional streaks of pink (2.5 R 7/6). Stamens approximately 30 in number, in random arrangement; anthers bright yellow (2.5 Y 8.5/12). Pistil: styles 5 to 8 in number, typical length in one observation 7 mm, fused at base; stigma medium length, rounded at top. Sepals, in one observation, typically 10 mm in length, 4 mm in width, dull green (2.5 GY 5/8), with fine, colorless pubescence.

Bloom fragrance: Light.

Showiness: Highly showy as bright pink buds open to typical semi-double to double white flowers.

Fertility: Self sterile, but capable of setting fruit on other apple varieties. Actual crosses were made with emasculated flowers of 'Jonagold', 'Braeburn', and 'McIntosh' (unpatented), resulting in fertilization and fruit set.

Pollen production: Heavy, due to prolific annual blooming habit.

Hardiness: Since this seedling originated in western Washington, an area lacking in extremes of temperature, the maximum hardiness is not known. Lowest temperature in the area was −14.4 degrees C. (6 degrees F.) in 1992. No injury to flower or tree was sustained that year.

Disease and insect resistance/susceptibility: This variety, in so far as has been observed, is apparently highly resistant, if not immune, to apple scab (*Venturia inaequalis*). No scab infection has been observed over 19 years on the original tree and on the second-generation trees planted at the WSU Research Unit. No fungicide control was applied to any of these trees. The new variety also appears resistant to powdery mildew. No confirmed infection has been noted over the past 5 years of observation at the WSU Research Unit in Mount Vernon, Wash.

I claim:

1. A new and distinct variety of crabapple tree named 'Jarmin' substantially as shown and described herein and characterized by the following combination of characteristics: non-fruiting, upright growth habit, resistance to apple scab and powdery mildew, attractive and prolific flowering habit.

* * * * *